US008026380B2

(12) United States Patent
Hassan et al.

(10) Patent No.: US 8,026,380 B2
(45) Date of Patent: Sep. 27, 2011

(54) SYSTEM AND PROCESS FOR PRODUCTION OF FATTY ACIDS AND WAX ALTERNATIVES FROM TRIGLYCERIDES

(75) Inventors: Abbas Hassan, Sugar Land, TX (US); Ebrahim Bagherzadeh, Sugar Land, TX (US); Rayford G. Anthony, College Station, TX (US); Gregory Borsinger, Chatham, NJ (US); Aziz Hassan, Sugar Land, TX (US)

(73) Assignee: H R D Corporation

(*) Notice: Subject to any disclaimer, the term of this patent is extended or adjusted under 35 U.S.C. 154(b) by 557 days.

(21) Appl. No.: 12/140,743

(22) Filed: Jun. 17, 2008

(65) Prior Publication Data

US 2009/0036694 A1 Feb. 5, 2009

Related U.S. Application Data

(60) Provisional application No. 60/952,682, filed on Jul. 30, 2007.

(51) Int. Cl.
*C07C 51/00* (2006.01)

(52) U.S. Cl. ........................................ 554/161; 422/198

(58) Field of Classification Search .................. 554/161; 422/198

See application file for complete search history.

(56) References Cited

U.S. PATENT DOCUMENTS

| | | | | |
|---|---|---|---|---|
| 1,998,997 | A * | 4/1935 | Tolman | 554/1 |
| 3,253,007 | A * | 5/1966 | Lunde | 554/160 |
| 3,634,201 | A | 1/1972 | Kehse | |
| 5,211,812 | A * | 5/1993 | Vielberth et al. | 202/172 |
| 5,877,350 | A | 3/1999 | Langer et al. | |
| 5,952,517 | A | 9/1999 | Ries et al. | |
| 6,368,366 | B1 | 4/2002 | Langer et al. | |
| 6,368,367 | B1 | 4/2002 | Langer et al. | |
| 6,383,237 | B1 | 5/2002 | Langer et al. | |
| 2003/0043690 | A1 | 3/2003 | Holl | |
| 2004/0052158 | A1 | 3/2004 | Holl | |
| 2004/0210070 | A1 * | 10/2004 | Kruidenberg | 554/205 |
| 2005/0033069 | A1 | 2/2005 | Holl et al. | |

FOREIGN PATENT DOCUMENTS

KR 10-0228888 B1 11/1999

OTHER PUBLICATIONS

Miura, K., et al.; "New Oxidative Degradation Method for Producing Fatty Acids in High Yields and High Selectivity from Low-Rank Coals," Energy & Fuels, (1996) vol. 10, No. 6, pp. 1196-1201.

International Search Report, International Application No. PCT/US2008/068169, dated Jan. 21, 2009.

* cited by examiner

*Primary Examiner* — Deborah D Carr

(74) *Attorney, Agent, or Firm* — Porter Hedges LLP; Timothy S. Westby

(57) ABSTRACT

A method of producing volatilized fatty acids by heating a feedstock comprising at least one fat or oil in a reactor under inert vacuum to volatilize fatty acids, and removing volatilized fatty acids from bottoms residue comprising cross-linked oil. A system for stripping fatty acids from triglycerides, the system comprising a reactor, heating apparatus and a vacuum pump capable of pulling a vacuum in the range of from 1 kPa to 50 kPa on the reactor. A system for producing a hydrogenated product including a reactor comprising an inlet for a stream comprising triglycerides, an outlet for volatilized fatty acids, and an outlet for a cross-linked product, heating apparatus, a vacuum pump capable of pulling a vacuum in the range of from 1 kPa to 50 kPa on the reactor, and a hydrogenation reactor, wherein an inlet of the hydrogenation reactor is fluidly connected to the outlet for cross-linked product.

13 Claims, 3 Drawing Sheets

SYSTEM AND PROCESS FOR PRODUCTION OF FATTY ACIDS AND WAX ALTERNATIVES FROM TRIGLYCERIDES

CROSS-REFERENCE TO RELATED APPLICATIONS

This application claims the benefit under 35 U.S.C. §119 (e) of U.S. Provisional Patent Application No. 60/952,682 entitled "Process for Production of Fatty Acids and Wax Alternatives from Triglycerides," filed Jul. 30, 2007 the disclosure of which is hereby incorporated herein by reference.

STATEMENT REGARDING FEDERALLY SPONSORED RESEARCH OR DEVELOPMENT

Not Applicable.

BACKGROUND OF THE INVENTION

1. Field of the Invention

This invention relates to a system and process for producing fatty acids and paraffinic wax alternatives from triglycerides derived from plants and animals. Specifically, the present invention relates to a process for cross-linking glycerol fatty acid ester-containing compositions, producing free fatty acids and separating free fatty acids from a cross-linked residue. The free fatty acids may be fractionated. The residual cross-linked 'bottoms' may be used as an additive to crude triglyceride prior to hydrogenation thereof. The hydrogenation of a blend of cross-linked bottoms with crude triglyceride possesses properties that render it suitable for use as a paraffinic wax substitute.

2. Background of the Invention

Oils extracted from vegetable seeds and produce such as soy, corn, rapeseed and the like consist primarily of triglycerides. Triglycerides are composed of a glycerin molecule combined with three fatty acids. The term "fatty acids" is commonly understood to refer to the carboxylic acids naturally found in animal fats, vegetable, and marine oils. The major difference between vegetable oils derived from different sources is in the fatty acid component of the triglycerides. Fatty acids can vary in the number of carbon atoms in the molecule and in the number of double bonds in the fatty acid. The majority of the fatty acids in vegetable oils have carbon numbers of from about 8 to about 20 carbons. Fatty acids with the same number of carbon atoms may have different degrees of unsaturation (different numbers of double bonds). For example, stearic acid contains no double bonds (i.e. it is saturated), while oleic acid, linoleic acid, and linolenic acid contain a single double bond, two double bonds, and three double bonds, respectively.

Fatty acids without double bonds are known as saturated fatty acids, while those with at least one double bond are known as unsaturated fatty acids. The most common saturated fatty acids are palmitic acid (16 carbons) and stearic acid (18 carbons). Oleic and linoleic acid (both containing 18 carbons) are the most common unsaturated fatty acids.

Trans fatty acids are unsaturated fatty acids that contain at least one double bond in the trans isomeric configuration. The trans double bond configuration results in a greater bond angle than the cis configuration. This results in a more extended fatty acid carbon chain more similar to that of saturated fatty acids rather than that of fatty acids comprising cis unsaturated double bonds. The conformation of the double bond(s) impacts the physical properties of a fatty acid. Fatty acids containing a trans double bond have the potential for closer packing or aligning of acyl chains, resulting in decreased mobility; hence fluidity is reduced when compared to fatty acids containing a cis double bond. Trans fatty acids are commonly produced by the partial hydrogenation of vegetable oils. Saturated fats and trans isomers of unsaturated fatty acids are undesirable as food product components, as there is some indication that they are unhealthy. Due to these health concerns with saturated fats and fats containing trans fat, low trans fat content is desirable when fats are to be consumed.

Triglycerides, also known as triacylglycerols, can by hydrolyzed to yield carboxylic acids and alcohols. Reaction products produced by the complete hydrolysis of a fat or oil molecule are one molecule of glycerol and three fatty acid molecules. This reaction proceeds via stepwise hydrolysis of the acyl groups on the glyceride, so that at any given time, the reaction mixture contains not only triglyceride, water, glycerol, and fatty acid, but also diglycerides and monoglycerides.

Fatty acids that are separated or split from the glycerine backbone of the triglyceride molecule are commonly used as is and/or as a raw material in a variety of industries including the food, cosmetics, pharmaceutical, and chemical industries.

Fatty acids may be split from the glycerine molecule by several means. Due to its favorable cost, a widely used commercial process for hydrolyzing fats and oils is a high-temperature steam treatment method known as the Colgate-Emery Steam Hydrolysis Process. This method, and modifications thereof, uses a countercurrent reaction of water and fat under high temperatures ranging from 240° C. to 315° C. and high pressures in the range of 4.93 MPa (700 psig) to 5.17 MPa (750 psig). In this method, a tower is used to mix the fat and water to increase the efficiency of the hydrolysis reaction. Typically, fat is introduced into the bottom of the tower with a high pressure feed pump. Water is introduced to the top portion of the tower at a ratio of 40%-50% of the weight of the fat. As the fat ascends though the descending water, a continuous oil-water interface is created. It is at this interface that the hydrolysis reaction occurs. Direct injection of high pressure steam raises the temperature to approximately 260° C. and the pressure is maintained at from 4.83 MPa (700 psig) to 4.93 MPa (715 psig). The increased pressure causes the boiling point of the water to increase, allowing for the use of higher temperatures, which results in the increase solubility of the water in the fat. The increased solubility of water provides for a more efficient hydrolysis reaction. This continuous, countercurrent, high pressure process allows for a split yield of 98%-99% efficiency in 2 to 3 hours. Further purification of the fatty acid product obtained by this method is often accomplished by separation, e.g. distillation.

Other methods of hydrolysis are also used to avoid by-product formation and unsaturated fat degradation which are associated with the high pressure-high temperature hydrolysis of unsaturated fats and oils. Such methods include the hydrolysis of unsaturated oils by splitting them with a base followed by acidulation or by enzymatic hydrolysis. Split yields are generally lower than that for the Colgate-Emery process under similar time conditions.

Hydrogenated vegetable oils that have been heavily hydrogenated have been used to replace petroleum waxes in such applications as candles, boxboard coatings and adhesives. Petroleum waxes in most of these applications have melting points in excess of 48° C. (120° F.). This minimum melting point is desirable in order to avoid melting of the petroleum wax in tropic or hot summer conditions or in such as applications as hot pour and seal hot melt adhesive applications.

Vegetable waxes derived from triglycerides may be hydrogenated to increase the melting point. The degree of hydrogenation is usually measured by the iodine value of the wax. Very low iodine values are required in order for the hydrogenated vegetable oil to have melting points in excess of 48° C. (120° F.). Additionally, when the melting point of a hydrogenated vegetable oil is increased it becomes harder as noted by the needle penetration value, a common test known to those experienced in the art. As the melting point and hardness of the vegetable wax increase due to additional hydrogenation, the wax becomes more brittle. Brittle waxes tend to crack on flexing and are not suitable for applications such as flexible packaging and adhesives. Use of low iodine value (IV) vegetable wax in candle applications is generally undesirable because the wax tends to crack on solidifying, which is aesthetically undesirable.

Efforts to hydrogenate triglycerides to provide for a less brittle more flexible high melting product have been reported. To overcome the deficiencies of low IV hydrogenated triglyceride wax, additives and/or diluents are typically used to modify the triglyceride wax and make it more flexible, less brittle and/or higher melting. Compounds that have been added include mono- and diglycerides, vinyl polymers, petroleum and microcrystalline waxes, styrene butadiene polymers, fatty acids, alpha olefins, and glycerin.

Some of the problems associated with prior art include undesirable burning characteristics of the additives used to impart flexibility in candle applications and the fact that conventional additives may not be renewable, leading to environmental concerns. Also the addition of additives to impart flexibility and increased melt point requires an additional mixing step that is undesirable due to the additional manufacturing involved.

Accordingly, there is still a need in the industry for a system and method of splitting fatty acids from triglycerides, thereby producing fatty acids that exhibit superior product appearance, texture, and/or stability, and to provide a method for its preparation whereby a co-product is obtained that can be utilized to enhance hydrogenation of oil. The co-product may be used to produce solid vegetable wax useful as an alternative to or admixture component with petroleum waxes.

SUMMARY

Herein disclosed is a method of producing volatilized fatty acids including heating a feedstock comprising at least one fat or oil in a reactor under inert vacuum to volatilize fatty acids, and removing volatilized fatty acids from bottoms residue comprising cross-linked oil. The feedstock may be selected from butterfat, cocoa butter, cocoa butter substitutes, illipe fat, kokum butter, milk fat, mowrah fat, phulwara butter, sal fat, shea fat, bomeo tallow, lard, lanolin, beef tallow, mutton tallow, other animal tallow, canola oil, castor oil, coconut oil, coriander oil, corn oil, cottonseed oil, hazelnut oil, hempseed oil, linseed oil, mango kernel oil, meadowfoam oil, Neatsfoot oil, olive oil, palm oil, palm kernel oil, palm olein, palm stearin, palm kernel olein, palm kernel stearin, peanut oil, rapeseed oil, rice bran oil, safflower oil, sasanqua oil, soybean oil, sunflower seed oil, tall oil, tsubaki oil, vegetable oils, marine oils, and combinations thereof. In embodiments, the feedstock comprises soybean oil. The feedstock may have an iodine value of greater than 70. The feedstock may further comprise at least one antioxidant. The at least one antioxidant may comprise ascorbyl palmitate and tocopherol.

The method may further comprise contacting the feedstock with a crosslinking catalyst during heating. Heating may be to a temperature in the range of from about 200° C. to about 600° C. The vacuum may be in the range of from 1.0 kPa to about 50 kPa. The method may further comprise condensing the volatilized fatty acids to obtain a fatty acid condensate. Water may be introduced into the reactor to promote hydrolysis. The method may further comprise fractionating the fatty acids. Removing volatilized fatty acids from bottoms residue may be performed with a wiped film evaporator. In embodiments, less than about 6 weight percent of the volatilized fatty acids are trans-isomers. Cross-linking also reduces the number of double bonds in the fatty acids as indicated by a lower iodine value thereby making the fatty acid more thermally stable.

Also disclosed herein is a method of producing a hydrogenated product, the method comprising hydrogenating the bottoms residue to produce an enhanced hydrogenated product. The bottoms residue may be mixed with from about 0 weight percent to about 99 weight percent of a base oil prior to hydrogenation. The enhanced hydrogenated product may be blended with from about 1 weight percent to about 99 weight percent of paraffinic wax to yield a blended wax. Other additives may also be used in the blend including stabilizers and modifiers including ethylene copolymers such as ethylene vinyl acetate and ethylene propylene copolymers. The enhanced hydrogenated product may remain colorless upon standing for a time greater than one week. Hydrogenating the bottoms residue may comprise subjecting a mixture containing bottoms residue and hydrogen gas to a shear rate of greater than about 20,000 $s^{-1}$. Hydrogenating the bottoms residue may comprise forming a dispersion comprising hydrogen-containing gas bubbles dispersed in a liquid phase comprising bottoms residue, wherein the bubbles have a mean diameter of less than 5.0 μm. In embodiments, forming the dispersion comprises contacting hydrogen-containing gas and the liquid phase in a high shear device, wherein the high shear device comprises at least one rotor, and wherein the at least one rotor is rotated at a tip speed of at least 22.9 m/s (4,500 ft/min) during formation of the dispersion. The high shear device may produce a local pressure of at least about 1034.2 MPa (150,000 psi) at the tip of the at least one rotor. The energy expenditure of the high shear device may be greater than 1000 W/$m^3$ during formation of the dispersion. A blended wax comprising enhanced hydrogenated product and petroleum wax is also disclosed.

Also disclosed is a system for stripping fatty acids from triglycerides, the system comprising a reactor, heating apparatus whereby the contents of the reactor may be heated to a temperature in the range of from 200° C. to 600° C., and a vacuum pump capable of pulling a vacuum in the range of from 1 kPa to 50 kPa on the reactor. The system may further comprise a fractionator adapted to fractionate fatty acids. The fractionator may be a wiped film evaporator. The reactor may comprise an inlet for a stream comprising triglycerides, an outlet for volatilized fatty acids, and an outlet for a bottoms residue. In embodiments, the system further comprises at least one high shear mixing device comprising at least one rotor and at least one stator separated by a shear gap, wherein the shear gap is the minimum distance between the at least one rotor and the at least stator, wherein the high shear mixing device is capable of producing a tip speed of the at least one rotor of greater than 22.9 m/s (4,500 ft/min), and wherein an inlet of the high shear device is fluidly connected to the bottoms residue outlet of the reactor.

A system for producing a hydrogenated product is disclosed, the system comprising a reactor comprising an inlet for a stream comprising triglycerides, an outlet for volatilized fatty acids, and an outlet for a cross-linked product, heating apparatus whereby the contents of the reactor may be heated to a temperature in the range of from 200° C. to 600° C., a vacuum pump capable of pulling a vacuum in the range of from 1 kPa to 50 kPa on the reactor, and a hydrogenation reactor, wherein an inlet of the hydrogenation reactor is fluidly connected to the outlet for cross-linked product. The system may further comprise a high shear device upstream of the hydrogenation reactor, wherein the high shear device comprises at least one rotor and at least one stator.

These and other embodiments and potential advantages will be apparent in the following detailed description and drawings.

BRIEF DESCRIPTION OF THE DRAWINGS

For a more detailed description of the preferred embodiment of the present invention, reference will now be made to the accompanying drawings, wherein.

NOTATION AND NOMENCLATURE

Figure 1:
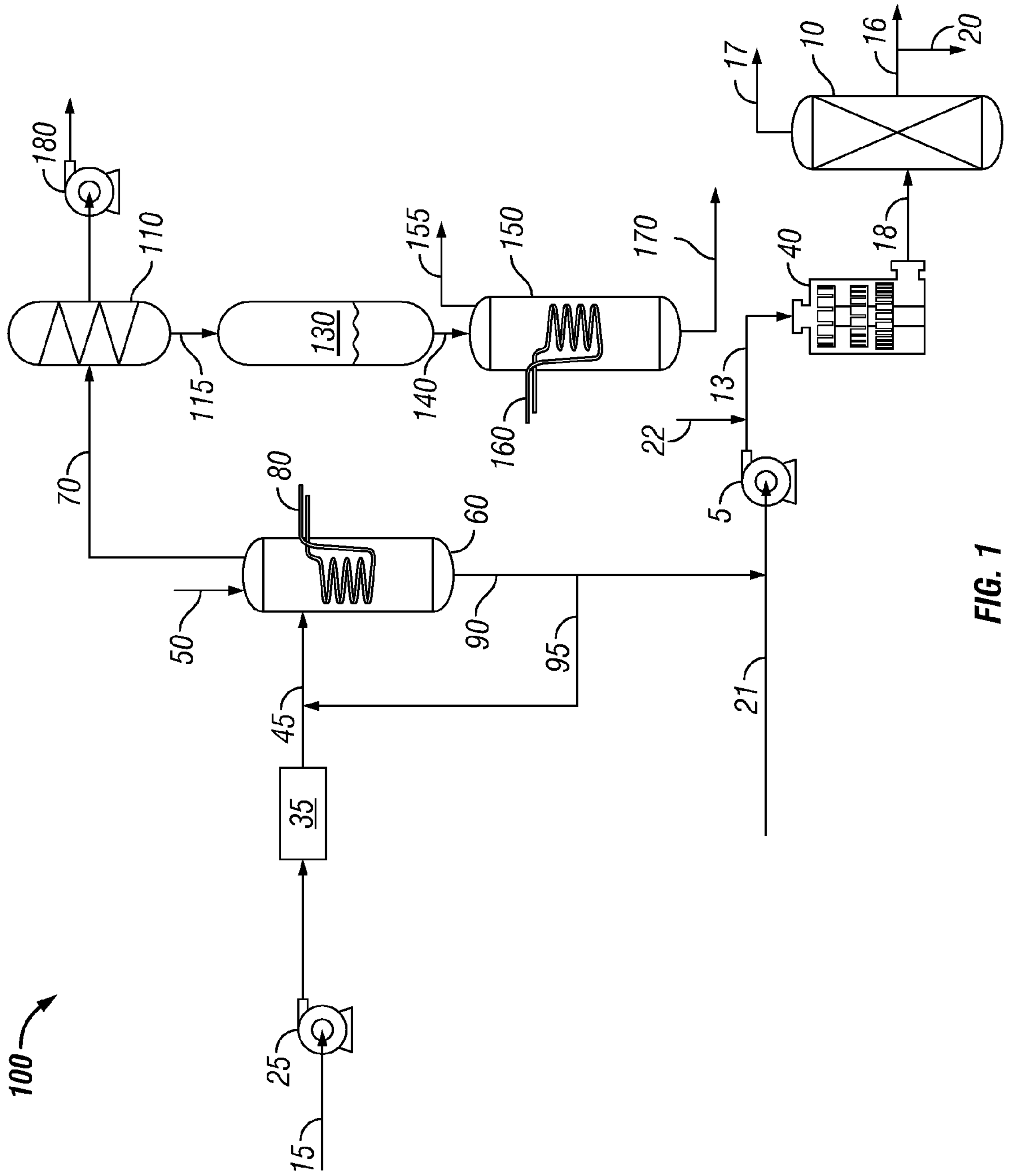
FIG. 1 is a schematic of a fatty acid production and crosslinking system according to an embodiment of the present invention.

Certain terms are used throughout the following description and claims to refer to particular system components. This document does not intend to distinguish between components that differ in name but not function. In the following discussion and in the claims, the terms "including" and "comprising" are used in an open-ended fashion, and thus should be interpreted to mean "including, but not limited to . . . ".

The term "fatty acid" as used herein is applied broadly to carboxylic acids ($C_6$ to $C_{20}$ typical) which are found in animal fats, vegetable and marine oils. Fatty acids can be found naturally in saturated, mono-unsaturated or poly-unsaturated forms. The natural geometric configuration of fatty acids is cis-isomer configuration. The cis-isomer configuration contributes significantly to the liquidity of these acids. The term "fatty acid" refers to the component of a triglyceride that is the long carbon chain components of the triglyceride. The chemical names and the number of carbon atoms and double bonds of common fatty acids are presented in Table 1.

As used herein the term "free fatty acid" refers to the vacuum stripped product obtained following heating of the fat at elevated temperatures under inert conditions.

TABLE 1

Fatty Acid Nomenclature

| No. Carbons-No. Double Bonds | Name |
|---|---|
| C8 | Octanoic Acid |
| C10 | Capric Acid |
| C12 | Lauric Acid |
| C14 | Myristic Acid |
| C15 | Pentadecanoic Acid |
| C15-1 | Pentadecanoic Acid |
| C16 | Palmitic Acid |
| C16-1 | Palmitoleic Acid |
| C17 | Heptadecanoic Acid |
| C17-1 | 10-Heptadecanoic Acid |
| C18 | Stearic Acid |
| C18-1 | Oleic Acid |
| C18-2 | Linoleic Acid |
| C18-3 | Linolenic Acid |
| C20 | Arachidic Acid |
| C20-1 | Eicosenoic Acid |
| C22 | Behenic Acid |
| C22-1 | Erucic Acid |
| C24 | Lignoceric Acid |

The term "saturates", "saturated fat", and "saturated fatty acids" as used herein refer to C4 to C26 fatty acids or esters containing no unsaturation unless otherwise indicated. The term "unsaturated" refers to the presence of at least one carbon-carbon double bond within the hydrocarbon chain.

The "iodine value" is a measure of the total number of unsaturated double bonds present in a fat or oil. The term "iodine value" or "IV" as used herein refers to the number of grams of iodine equivalent to halogen adsorbed by a 100 gram sample of fat.

The phrase "high in unsaturated fats" includes fats and oils, or mixtures thereof, with an iodine value of greater than 110 as determined by the Wijs method.

The term "trans", "trans fatty acids," "trans isomers" and "trans isomers of fatty acids" as used herein refer to fatty acids and/or esters containing double bonds in the trans configuration usually resulting from hydrogenation or partial hydrogenation of a fat. In low trans fat or oil, less than about 6 weight percent of the total fatty acid composition comprises trans fat.

The terms "fat" and "oil" as used herein are intended to include all edible, fatty acid triglycerides regardless of origin or whether they are solid or liquid at room temperature. Thus, the term "fat" and the term "oil" include normally liquid and normally solid vegetable and animal fats and oils. Natural and synthetic fats and oils are included in these terms.

The term "edible oil" or "base oil" as used herein refers to oil which is substantially liquid at room temperature and has an IV of greater than 70, more preferably greater than 100. The base oil can be unhydrogenated oil or partially hydrogenated oil, modified oil (e.g., bleached and/or deodorized) or mixtures thereof.

As used herein "hydrolysis" refers to the separation of a glycerol fatty acid ester-containing composition, such as a fat or oil starting material, into its fatty acid and glycerin components by reacting the starting material with water.

As used herein, the term "dispersion" refers to a liquefied mixture that contains at least two distinguishable substances (or "phases") that will not readily mix and dissolve together. As used herein, a "dispersion" comprises a "continuous" phase (or "matrix"), which holds therein discontinuous droplets, bubbles, and/or particles of the other phase or substance. The term dispersion may thus refer to foams comprising gas bubbles suspended in a liquid continuous phase, emulsions in which droplets of a first liquid are dispersed throughout a continuous phase comprising a second liquid with which the first liquid is immiscible, and continuous liquid phases throughout which solid particles are distributed. As used herein, the term "dispersion" encompasses continuous liquid phases throughout which gas bubbles are distributed, continuous liquid phases throughout which solid particles (e.g., solid catalyst) are distributed, continuous phases of a first liquid throughout which droplets of a second liquid that is substantially insoluble in the continuous phase are distributed, and liquid phases throughout which any one or a combination of solid particles, immiscible liquid droplets, and gas bubbles are distributed. Hence, a dispersion can exist as a homogeneous mixture in some cases (e.g., liquid/liquid phase), or as a heterogeneous mixture (e.g., gas/liquid, solid/liquid, or gas/solid/liquid), depending on the nature of the materials selected for combination.

DETAILED DESCRIPTION

Overview. Herein disclosed are a system and process for processing triglyceride oil to produce stable fatty acids and create residual bottoms (hereinafter BCR-bottoms cross-linked residue) useful as a modifier for the production of enhanced vegetable oil waxes.

Figure 2:
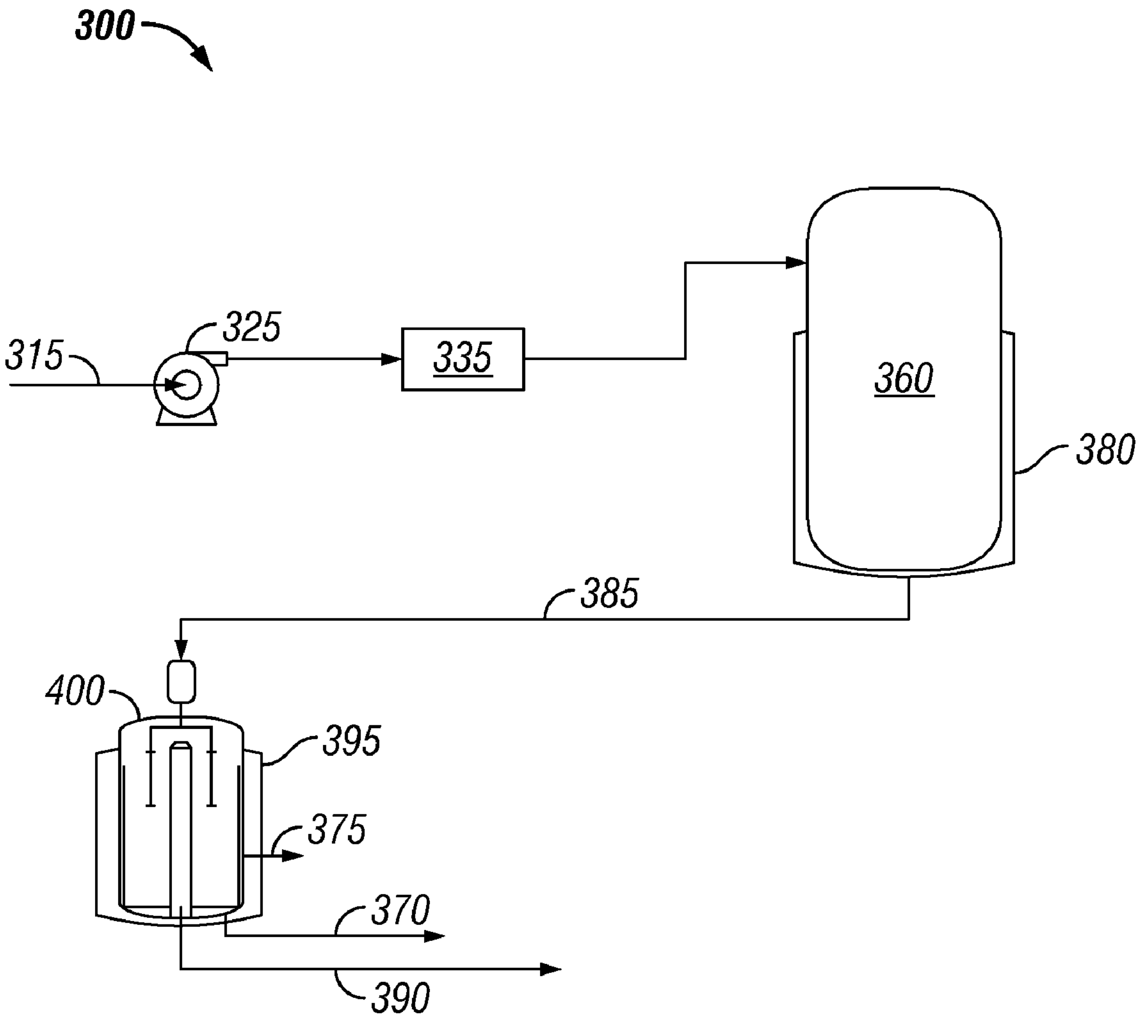
FIG. 2 is a schematic of a fatty acid production and crosslinking system comprising a wiped film evaporator according to another embodiment of the present invention.

System for Production of Fatty Acids and Wax Alternatives from Triglycerides. The system and process of the present disclosure utilize primarily heat and vacuum to split and separate fatty acids followed by fractionation to isolate various chain length components. FIG. 1 is a process flow diagram of a fatty acid production and cross-linking system 100 according to an embodiment of the present disclosure. The basic components of a representative system 100 include reactor 60, condenser 110, and vacuum pump 180. Reactor 60 comprises heating apparatus 80, which may be, for example, an internal heat exchanger, a heating mantle, or other known heating apparatus adapted to heat the contents of reactor 60. In embodiments, reactor 60 is operated as a batch reactor, and comprises no liquid inlet or liquid outlet. In other embodiments, system 100 is designed for continuous operation, and reactor 60 is connected to inlet line 45 for introducing triglyceride into reactor 60 and outlet line 90 for removing bottoms product from reactor 60. An outlet line 70 may be used to extract product gas comprising volatilized fatty acids from reactor 60. In other embodiments, as shown in the embodiment of FIG. 2, reactor 360 is not fluidly connected to a gas outlet line. Inlet line 50 may be used to introduce inert gas into reactor 60.

Condenser 110 is any apparatus suitable for liquefying the volatilized fatty acids produced in reactor 60. System 100 may further comprise an accumulator 130 for accumulation of condensate comprising liquid fatty acids. An outlet line 115 from condenser 110 may introduce liquefied fatty acid product into accumulator 130. Vacuum pump 180 is any suitable vacuum pump for pulling a vacuum on condenser 110 and reactor 60.

System 100 may further comprise pump 25 and heater 35 which may respectively pump and heat feedstock comprising triglyceride from line 15 into reactor 60. In embodiments, system 100 further comprises apparatus for fractionating the fatty acids produced in reactor 60. For example, in the embodiment of FIG. 1, system 100 further comprises fractionator 150, fluidly connected to condenser 110 via line 140, accumulator 130, and line 115. By adjusting the temperature of fractionator 150 via, for example, internal heat exchanger 160, lower boiling fatty acids may be removed in overhead line 155 and higher boiling fatty acids may be removed via line 170.

FIG. 2 is a process flow diagram of a fatty acid production and cross-linking system 300 according to another embodiment of the present disclosure. In the embodiment of FIG. 2, system 300 comprises reactor 360 and wiped film evaporator 400 via reactor outlet line 385. In this embodiment, product from reactor 360 is introduced into a wiped film evaporator 400. In this embodiment, reactor 360 serves primarily as a heated holding tank and comprises heating apparatus, 380, which is indicated in FIG. 2 as a heating mantle. Pump 325 and heater 335 may be used, respectively, to pump and preheat feedstock comprising triglyceride in line 315 prior to introduction into reactor 360. In the embodiment of FIG. 2, wiped film evaporator 400 is used to fractionate and separate the fatty acids produced in reactor 360 from residual bottoms cross-linked product. Fractionated fatty acids may exit WFE 400 via line 370, while BCR may exit WFE 400 via line 390. A vacuum pump (not shown) may be used to pull a desired vacuum on the contents of wiped film evaporator 400, via line 375. An outlet line 370 may be connected to WFE 400 for removal of fractionated fatty acids, and an outlet 390 may be connected to WFE 400 for removal of bottoms cross-linked residue from WFE 400. Wiped film evaporators can be operated at fractional mm of Hg and temperatures up to about 400° C. depending on the heating fluid utilized in heat exchanger 395.

Referring again to FIG. 1, outlet line 90 may be fluidly connected with line 15 for multiple pass operation, as discussed further hereinbelow.

In embodiments, system 100 further comprises hydrogenation apparatus for hydrogenating at least a portion of the bottoms cross-linked residue. For example, in the embodiment of FIG. 1, system 100 further comprises pump 5, external high shear mixing device (HSD) 40, and vessel 10. As shown in FIG. 1, high shear device 40 is located external to vessel/reactor 10. Each of these components is further described in more detail below. Line 21 may be connected to pump 5 for introducing additional oil or fat to be hydrogenated. Line 13 connects pump 5 to HSD 40, and line 18 connects HSD 40 to vessel 10. Line 22 may be connected to line 13 for introducing a hydrogen-containing gas (e.g., $H_2$). Alternatively, line 22 may be connected to an inlet of HSD 40. Line 17 may be connected to vessel 10 for removal of unreacted hydrogen and/or other reaction or product gases.

Additional components or process steps may be incorporated throughout system 100, if desired, as will become apparent upon reading the description of the process described hereinbelow. For example, a line 20 may be connected to line 21 or line 13, to provide for looping around HSD 40, if desired.

High Shear Mixing Device. External high shear mixing device (HSD) 40, also sometimes referred to as a high shear device or high shear mixing device, is configured for receiving an inlet stream, via line 13, comprising oil to be hydrogenated and molecular hydrogen. Alternatively, HSD 40 may be configured for receiving the liquid and gaseous reactant streams via separate inlet lines (not shown). Although only one high shear device is shown in FIG. 1, it should be understood that some embodiments of the system may have two or more high shear mixing devices arranged either in series or parallel flow. HSD 40 is a mechanical device that utilizes one or more generators comprising a rotor/stator combination, each of which has a gap between the stator and rotor. The gap between the rotor and the stator in each generator set may be fixed or may be adjustable. HSD 40 is configured in such a way that it is capable of producing submicron and micron-sized bubbles in a reactant mixture flowing through the high shear device. The high shear device comprises an enclosure or housing so that the pressure and temperature of the reaction mixture may be controlled.

High shear mixing devices are generally divided into three general classes, based upon their ability to mix fluids. Mixing is the process of reducing the size of particles or inhomogeneous species within the fluid. One metric for the degree or thoroughness of mixing is the energy density per unit volume that the mixing device generates to disrupt the fluid particles. The classes are distinguished based on delivered energy densities. Three classes of industrial mixers having sufficient energy density to consistently produce mixtures or emulsions with particle sizes in the range of submicron to 50 microns include homogenization valve systems, colloid mills and high speed mixers. In the first class of high energy devices, referred to as homogenization valve systems, fluid to be processed is pumped under very high pressure through a narrow-gap valve into a lower pressure environment. The pressure gradients across the valve and the resulting turbulence and cavitation act to break-up any particles in the fluid. These valve systems are most commonly used in milk homogenization and can yield average particle sizes in the submicron to about 1 micron range.

At the opposite end of the energy density spectrum is the third class of devices referred to as low energy devices. These systems usually have paddles or fluid rotors that turn at high speed in a reservoir of fluid to be processed, which in many of the more common applications is a food product. These low energy systems are customarily used when average particle sizes of greater than 20 microns are acceptable in the processed fluid.

Between the low energy devices and homogenization valve systems, in terms of the mixing energy density delivered to the fluid, are colloid mills and other high speed rotor-stator devices, which are classified as intermediate energy devices. A typical colloid mill configuration includes a conical or disk rotor that is separated from a complementary, liquid-cooled stator by a closely-controlled rotor-stator gap, which is commonly between 0.0254 mm to 10.16 mm (0.001-0.40 inch). Rotors are usually driven by an electric motor through a direct drive or belt mechanism. As the rotor rotates at high rates, it pumps fluid between the outer surface of the rotor and the inner surface of the stator, and shear forces generated in the gap process the fluid. Many colloid mills with proper adjustment achieve average particle sizes of 0.1-25 microns in the processed fluid. These capabilities render colloid mills appropriate for a variety of applications including colloid and oil/water-based emulsion processing such as that required for cosmetics, mayonnaise, or silicone/silver amalgam formation, to roofing-tar mixing.

Tip speed is the circumferential distance traveled by the tip of the rotor per unit of time. Tip speed is thus a function of the rotor diameter and the rotational frequency. Tip speed (in meters per minute, for example) may be calculated by multiplying the circumferential distance transcribed by the rotor tip, 2 $\pi R$, where R is the radius of the rotor (meters, for example) times the frequency of revolution (for example revolutions per minute, rpm). A colloid mill, for example, may have a tip speed in excess of 22.9 m/s (4500 ft/min) and may exceed 40 m/s (7900 ft/min). For the purpose of this disclosure, the term 'high shear' refers to mechanical rotor stator devices (e.g., colloid mills or rotor-stator dispersers) that are capable of tip speeds in excess of 5.1 m/s. (1000 ft/min) and require an external mechanically driven power device to drive energy into the stream of products to be reacted. For example, in HSD 40, a tip speed in excess of 22.9 m/s (4500 ft/min) is achievable, and may exceed 40 m/s (7900 ft/min). In some embodiments, HSD 40 is capable of delivering at least 300 L/h at a tip speed of at least 22.9 m/s (4500 ft/min). The power consumption may be about 1.5 kW. HSD 40 combines high tip speed with a very small shear gap to produce significant shear on the material being processed. The amount of shear will be dependent on the viscosity of the fluid. Accordingly, a local region of elevated pressure and temperature is created at the tip of the rotor during operation of the high shear device. In some cases the locally elevated pressure is about 1034.2 MPa (150,000 psi). In some cases the locally elevated temperature is about 500° C. In some cases, these local pressure and temperature elevations may persist for nano or pico seconds.

An approximation of energy input into the fluid (kW/L/min) can be estimated by measuring the motor energy (kW) and fluid output (L/min). As mentioned above, tip speed is the velocity (ft/min or m/s) associated with the end of the one or more revolving elements that is creating the mechanical force applied to the reactants. In embodiments, the energy expenditure of HSD 40 is greater than 1000 W/$m^3$. In embodiments, the energy expenditure of HSD 40 is in the range of from about 3000 W/$m^3$ to about 7500 W/$m^3$.

The shear rate is the tip speed divided by the shear gap width (minimal clearance between the rotor and stator). The shear rate generated in HSD 40 may be in the greater than 20,000 $s^{-1}$. In some embodiments the shear rate is at least 40,000 $s^{-1}$. In some embodiments the shear rate is at least 100,000 $s^{-1}$. In some embodiments the shear rate is at least 500,000 $s^{-1}$. In some embodiments the shear rate is at least 1,000,000 $s^{-1}$. In some embodiments the shear rate is at least 1,600,000 $s^{-1}$. In embodiments, the shear rate generated by HSD 40 is in the range of from 20,000 $s^{-1}$ to 100,000 $s^{-1}$. For example, in one application the rotor tip speed is about 40 m/s (7900 ft/min) and the shear gap width is 0.0254 mm (0.001 inch), producing a shear rate of 1,600,000 $s^{-1}$. In another application the rotor tip speed is about 22.9 m/s (4500 ft/min) and the shear gap width is 0.0254 mm (0.001 inch), producing a shear rate of about 901,600 $s^{-1}$.

HSD 40 is capable of highly dispersing or transporting hydrogen into a main liquid phase (continuous phase) comprising unsaturated triglycerides, with which it would normally be immiscible, at conditions such that at least a portion of the hydrogen reacts with the triglyceride to produce a product stream comprising enhanced hydrogenated product. In embodiments, the unsaturated hydrogenation feedstream further comprises a catalyst. In some embodiments, HSD 40 comprises a colloid mill. Suitable colloidal mills are manufactured by IKA® Works, Inc. Wilmington, N.C. and APV North America, Inc. Wilmington, Mass., for example. In some instances, HSD 40 comprises the Dispax Reactor® of IKA® Works, Inc.

The high shear device comprises at least one revolving element that creates the mechanical force applied to the reactants. The high shear device comprises at least one stator and at least one rotor separated by a clearance. For example, the rotors may be conical or disk shaped and may be separated from a complementarily-shaped stator. In embodiments, both the rotor and stator comprise a plurality of circumferentially-spaced teeth. In some embodiments, the stator(s) are adjustable to obtain the desired shear gap between the rotor and the stator of each generator (rotor/stator set). Grooves between the teeth of the rotor and/or stator may alternate direction in alternate stages for increased turbulence. Each generator may be driven by any suitable drive system configured for providing the necessary rotation.

In some embodiments, the minimum clearance (shear gap width) between the stator and the rotor is in the range of from about 0.0254 mm (0.001 inch) to about 3.175 mm (0.125 inch). In certain embodiments, the minimum clearance (shear gap width) between the stator and rotor is about 1.52 mm (0.060 inch). In certain configurations, the minimum clearance (shear gap) between the rotor and stator is at least 1.78 mm (0.07 inch). The shear rate produced by the high shear device may vary with longitudinal position along the flow pathway. In some embodiments, the rotor is set to rotate at a speed commensurate with the diameter of the rotor and the desired tip speed. In some embodiments, the high shear device has a fixed clearance (shear gap width) between the stator and rotor. Alternatively, the high shear device has adjustable clearance (shear gap width).

In some embodiments, HSD 40 comprises a single stage dispersing chamber (i.e., a single rotor/stator combination, a single generator). In some embodiments, high shear device 40 is a multiple stage inline disperser and comprises a plurality of generators. In certain embodiments, HSD 40 comprises at least two generators. In other embodiments, high shear device 40 comprises at least 3 high shear generators. In some embodiments, high shear device 40 is a multistage mixer whereby the shear rate (which, as mentioned above, varies proportionately with tip speed and inversely with rotor/stator gap width) varies with longitudinal position along the flow pathway, as further described herein below.

In some embodiments, each stage of the external high shear device has interchangeable mixing tools, offering flexibility. For example, the DR 2000/4 Dispax Reactor® of IKA® Works, Inc. Wilmington, N.C. and APV North America, Inc. Wilmington, Mass., comprises a three stage dispersing module. This module may comprise up to three rotor/stator combinations (generators), with choice of fine, medium, coarse, and super-fine for each stage. This allows for creation of dispersions having a narrow distribution of the desired bubble size (e.g., hydrogen gas bubbles). In some embodiments, each of the stages is operated with super-fine generator. In some embodiments, at least one of the generator sets has a rotor/stator minimum clearance (shear gap width) of greater than about 5.08 mm (0.20 inch). In alternative embodiments, at least one of the generator sets has a minimum rotor/stator clearance of greater than about 1.78 mm (0.07 inch).

Figure 3:
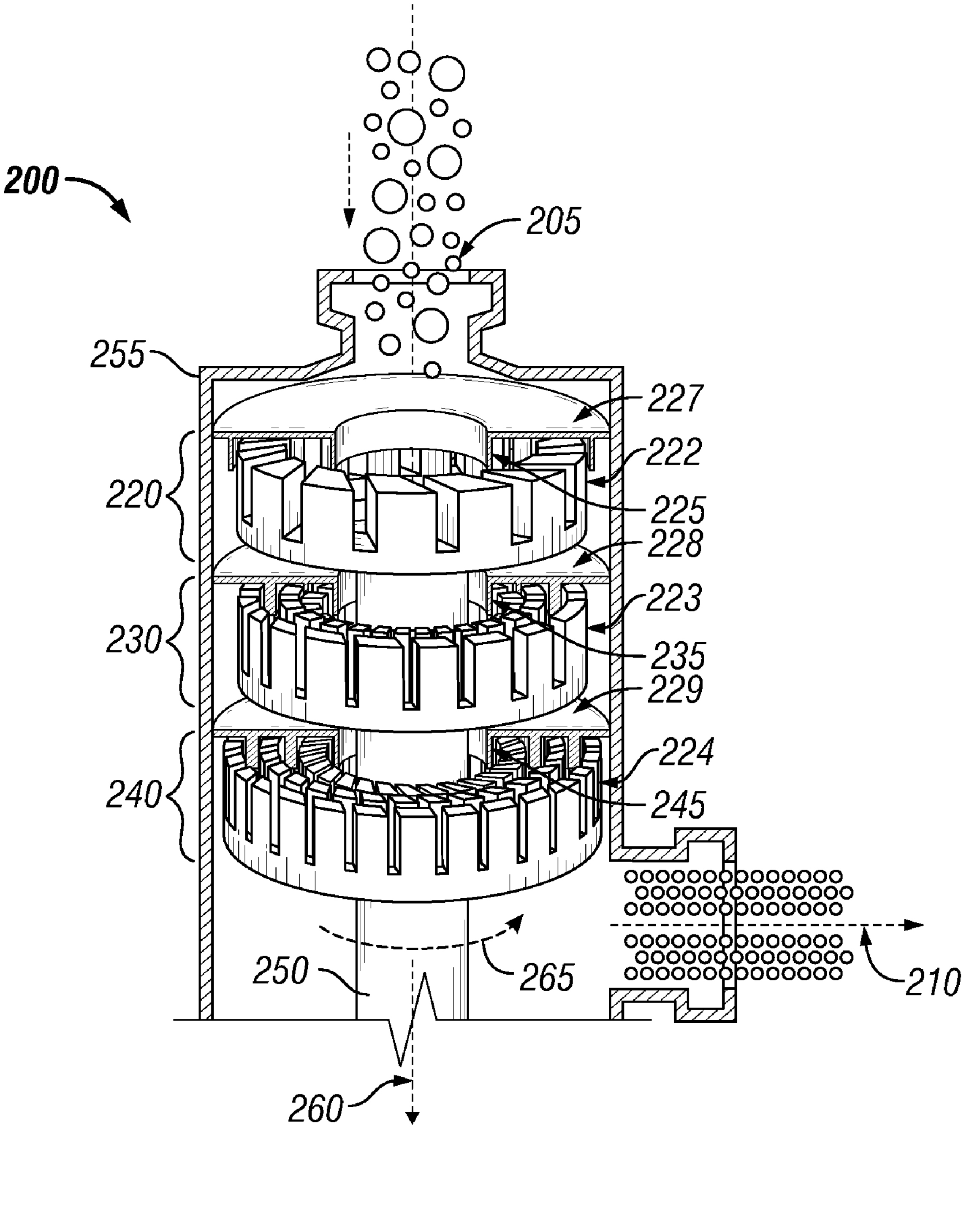
FIG. 3 is a longitudinal cross-section view of a multi-stage high shear device, as employed in an embodiment of the system.

Referring now to FIG. 3, there is presented a longitudinal cross-section of a suitable high shear device 200. High shear device 200 of FIG. 3 is a dispersing device comprising three stages or rotor-stator combinations. High shear device 200 is a dispersing device comprising three stages or rotor-stator combinations, 220, 230, and 240. The rotor-stator combinations may be known as generators 220, 230, 240 or stages without limitation. Three rotor/stator sets or generators 220, 230, and 240 are aligned in series along drive shaft 250.

First generator 220 comprises rotor 222 and stator 227. Second generator 230 comprises rotor 223, and stator 228. Third generator 240 comprises rotor 224 and stator 229. For each generator the rotor is rotatably driven by input 250 and rotates about axis 260 as indicated by arrow 265. The direction of rotation may be opposite that shown by arrow 265 (e.g., clockwise or counterclockwise about axis of rotation 260). Stators 227, 228, and 229 are fixably coupled to the wall 255 of high shear device 200.

As mentioned hereinabove, each generator has a shear gap width which is the minimum distance between the rotor and the stator. In the embodiment of FIG. 3, first generator 220 comprises a first shear gap 225; second generator 230 comprises a second shear gap 235; and third generator 240 comprises a third shear gap 245. In embodiments, shear gaps 225, 235, 245 have widths in the range of from about 0.025 mm to about 10.0 mm. Alternatively, the process comprises utilization of a high shear device 200 wherein the gaps 225, 235, 245 have a width in the range of from about 0.5 mm to about 2.5 mm. In certain instances the shear gap width is maintained at about 1.5 mm. Alternatively, the width of shear gaps 225, 235, 245 are different for generators 220, 230, 240. In certain instances, the width of shear gap 225 of first generator 220 is greater than the width of shear gap 235 of second generator 230, which is in turn greater than the width of shear gap 245 of third generator 240. As mentioned above, the generators of each stage may be interchangeable, offering flexibility. High shear device 200 may be configured so that the shear rate will increase stepwise longitudinally along the direction of the flow 260.

Generators 220, 230, and 240 may comprise a coarse, medium, fine, and super-fine characterization. Rotors 222, 223, and 224 and stators 227, 228, and 229 may be toothed designs. Each generator may comprise two or more sets of rotor-stator teeth. In embodiments, rotors 222, 223, and 224 comprise more than 10 rotor teeth circumferentially spaced about the circumference of each rotor. In embodiments, stators 227, 228, and 229 comprise more than ten stator teeth circumferentially spaced about the circumference of each stator. In embodiments, the inner diameter of the rotor is about 12 cm. In embodiments, the diameter of the rotor is about 6 cm. In embodiments, the outer diameter of the stator is about 15 cm. In embodiments, the diameter of the stator is about 6.4 cm. In some embodiments the rotors are 60 mm and the stators are 64 mm in diameter, providing a clearance of about 4 mm. In certain embodiments, each of three stages is operated with a super-fine generator, comprising a shear gap of between about 0.025 mm and about 4 mm. For applications in which solid particles are to be sent through high shear device 40, the appropriate shear gap width (minimum clearance between rotor and stator) may be selected for an appropriate reduction in particle size and increase in particle surface area. In embodiments, this may be beneficial for increasing catalyst surface area by shearing and dispersing the particles.

High shear device 200 is configured for receiving from line 13 a reactant mixture at inlet 205. The reaction mixture comprises hydrogen as the dispersible phase and unsaturated (or partially saturated) hydrogenation feed as the continuous phase. The feed stream may further comprise a particulate solid catalyst component. Feed stream entering inlet 205 is pumped serially through generators 220, 230, and then 240, such that product dispersion is formed. Product dispersion exits high shear device 200 via outlet 210 (and line 18 of FIG. 1). The rotors 222, 223, 224 of each generator rotate at high speed relative to the fixed stators 227, 228, 229, providing a high shear rate. The rotation of the rotors pumps fluid, such as the feed stream entering inlet 205, outwardly through the shear gaps (and, if present, through the spaces between the rotor teeth and the spaces between the stator teeth), creating a localized high shear condition. High shear forces exerted on fluid in shear gaps 225, 235, and 245 (and, when present, in the gaps between the rotor teeth and the stator teeth) through which fluid flows process the fluid and create product dispersion. Product dispersion exits high shear device 200 via high shear outlet 210 (and line 18 of FIG. 1).

The product dispersion has an average hydrogen gas bubble size less than about 5 μm. In embodiments, HSD 40 produces a dispersion having a mean bubble size of less than about 1.5 μm. In embodiments, HSD 40 produces a dispersion having a mean bubble size of less than 1 μm; preferably the bubbles are sub-micron in diameter. In certain instances, the average bubble size is from about 0.1 μm to about 1.0 μm. In embodiments, HSD 40 produces a dispersion having a mean bubble size of less than 400 nm. In embodiments, HSD 40 produces a dispersion having a mean bubble size of less than 100 nm. High shear device 200 produces a dispersion comprising gas bubbles capable of remaining dispersed at atmospheric pressure for at least about 15 minutes.

Not to be limited by theory, it is known in emulsion chemistry that sub-micron particles, or bubbles, dispersed in a liquid undergo movement primarily through Brownian motion effects. The bubbles in the product dispersion created by high shear device 200 may have greater mobility through boundary layers of solid catalyst particles, thereby facilitating and accelerating the catalytic reaction through enhanced transport of reactants.

In certain instances, high shear device 200 comprises a Dispax Reactor® of IKA® Works, Inc. Wilmington, N.C. and APV North America, Inc. Wilmington, Mass. Several models are available having various inlet/outlet connections, horsepower, tip speeds, output rpm, and flow rate. Selection of the high shear device will depend on throughput requirements and desired particle or bubble size in dispersion in line 18 (FIG. 1) exiting outlet 210 of high shear device 200. IKA® model DR 2000/4, for example, comprises a belt drive, 4M generator, PTFE sealing ring, inlet flange 25.4 mm (1 inch) sanitary clamp, outlet flange 19 mm (¾ inch) sanitary clamp, 2HP power, output speed of 7900 rpm, flow capacity (water) approximately 300-700 L/h (depending on generator), a tip speed of from 9.4-41 m/s (1850 ft/min to 8070 ft/min).

Vessel. Vessel or reactor 10 is any type of vessel in which hydrogenation can propagate. For instance, a continuous or semi-continuous stirred tank reactor, or one or more batch reactors may be employed in series or in parallel. In some applications vessel 10 may be a tower reactor, and in others a tubular reactor or multi-tubular reactor. Any number of reactor inlet lines is envisioned, with one shown in FIG. 1 (line 18). An inlet line (not shown in FIG. 1) may be used to introduce a catalyst or catalyst slurry to vessel 10 in certain embodiments. Vessel 10 may comprise an exit line 17 for vent gas, and an outlet product line 16 for a hydrogenated product stream. In embodiments, vessel 10 comprises a plurality of reactor product lines 16.

Hydrogenation reactions will occur whenever suitable time, temperature and pressure conditions exist. In this sense hydrogenation could occur wherever temperature and pressure conditions are suitable. Where a circulated slurry based catalyst is utilized, reaction is more likely to occur at points outside vessel 10 shown of FIG. 1. Nonetheless a discrete reactor/vessel 10 is often desirable to allow for increased residence time, agitation and heating and/or cooling. When reactor 10 is utilized, the reactor/vessel 10 may be a fixed bed reactor, a fluidized bed reactor, or a transport bed reactor and may become the primary location for the hydrogenation reaction to occur due to the presence of catalyst and its effect on the rate of hydrogenation.

Thus, vessel 10 may be any type of reactor in which hydrogenation may propagate. For example, vessel 10 may comprise one or more tank or tubular reactor in series or in parallel. The hydrogenation reaction may be a homogeneous catalytic reaction in which the catalyst is in the same phase as another component of the reaction mixture or a heterogeneous catalytic reaction involving a solid catalyst. When vessel 10 is utilized, vessel 10 may be operated as slurry reactor, fixed bed reactor, trickle bed reactor, fluidized bed reactor, bubble column, or other method known to one of skill in the art.

Vessel 10 may include one or more of the following components: stirring system, heating and/or cooling capabilities, pressure measurement instrumentation, temperature measurement instrumentation, one or more injection points, and level regulator (not shown), as are known in the art of reaction vessel design. For example, a stirring system may include a motor driven mixer. A heating and/or cooling apparatus may comprise, for example, a heat exchanger. Alternatively, as much of the conversion reaction may occur within HSD 40 in some embodiments, vessel 10 may serve primarily as a storage vessel in some cases. Although generally less desired, in some applications vessel 10 may be omitted, particularly if multiple high shear devices/reactors are employed in series, as further described below.

Heat Transfer Devices. In addition to the above-mentioned heating/cooling capabilities of vessel 10, heater 35 (335 in FIG. 2) and reactor 60 (360 in FIG. 2), other external or internal heat transfer devices for heating or cooling a process stream are also contemplated in variations of the embodiments illustrated in FIG. 1. For example, heat may be added to or removed from vessel 10 via any method known to one skilled in the art. The use of external heating and/or cooling heat transfer devices is also contemplated. Some suitable locations for one or more such heat transfer devices are between pump 5 and HSD 40, between HSD 40 and vessel 10, and between vessel 10 and pump 5 when the high shear hydrogenation is operated in multi-pass mode. Some non-limiting examples of such heat transfer devices are shell, tube, plate, and coil heat exchangers, as are known in the art.

Pumps. Vacuum pumps 180 (FIG. 1) and 370 (FIG. 2) are any pumps suitable for pulling the desired vacuum on reactor 60 or WFE 400 respectively. In embodiments, vacuum pump 180 (370) is capable of pulling a vacuum in the range of 1 kPa and 50 kPa on reactor 60 (WFE 400).

Pump 5 is configured for either continuous or semi-continuous operation, and may be any suitable pumping device that is capable of providing greater than 202.65 kPa (2 atm) pressure, preferably greater than 303.975 kPa (3 atm) pressure, to allow controlled flow through HSD 40. For example, a Roper Type 1 gear pump, Roper Pump Company (Commerce Ga.) Dayton Pressure Booster Pump Model 2P372E, Dayton Electric Co (Niles, Ill.) is one suitable pump. Preferably, all contact parts of the pump comprise stainless steel, for example, 316 stainless steel. In some embodiments of the system, pump 5 is capable of pressures greater than about 2026.5 kPa (20 atm). In addition to pump 5, one or more additional, high pressure pump (not shown) may be included in the systems illustrated in FIGS. 1 and 2. For example, a booster pump, which may be similar to pump 5, may be included between HSD 40 and vessel 10 for boosting the pressure into vessel 10, or a recycle pump may be positioned on line 17 for recycling gas from vessel 10 to HSD 40. As another example, a supplemental feed pump, which may be similar to pump 5, may be included Pump 25 (325 in FIG. 2) is any pump suitable to introduce liquid feed from line 15 (315 in FIG. 2) into reactor 60 (360 in FIG. 2).

Production of Fatty Acids and Wax Alternatives from Triglycerides. Description of a process for producing fatty acids and wax alternatives from triglycerides will now be made with reference to FIG. 1. Feedstock comprising triglycerides may be pumped via pump 25 from line 15 to reactor 60. Heater 35 may be used to preheat the feedstream comprising triglycerides.

The starting materials that may be used in this invention vary widely. For purposes herein, starting materials include one or more refined or unrefined, bleached or unbleached and/or deodorized or non-deodorized fats and/or oils. The fats and oils may comprise a single fat or oil or combinations of more than one fat and/or oil. The starting triglyceride oil or fat in the feedstream (hereinafter referred to as "base oil") comprises non-hydrogenated and/or partially hydrogenated oil. The fats and oils may be saturated, mono-unsaturated or poly-unsaturated or any combination thereof. The base oil may be selected from the group consisting of fish oils, animal oils, vegetable oils, synthetic oils, genetically-modified plant oils, and derivatives and mixtures thereof. In embodiments, the base oil comprises vegetable oil. In a preferred embodiment, the starting material is mono-unsaturated or poly-unsaturated vegetable oil. In a particularly preferred embodiment, the starting material is a poly-unsaturated vegetable oil. In embodiments, the starting triglyceride base oil is a refined, bleached and deodorized (RBD) vegetable oil. In embodiments, the base oil starting triglyceride comprises vegetable oil selected from the group consisting of high erucic acid rapeseed, soybean, safflower, canola, castor, sunflower and linseed oils.

The feedstream in line 15 (315 in FIG. 2) may comprise one or more selected from butterfat, cocoa butter, cocoa butter substitutes, illipe fat, kokum butter, milk fat, mowrah fat, phulwara butter, sal fat, shea fat, bomeo tallow, lard, lanolin, beef tallow, mutton tallow, tallow or other animal fat, canola oil, castor oil, coconut oil, coriander oil, corn oil, cottonseed oil, hazelnut oil, hempseed oil, linseed oil, mango kernel oil, meadowfoam oil, Neatsfoot oil, olive oil, palm oil, palm kernel oil, palm olein, palm stearin, palm kernel olein, palm kernel stearin, peanut oil, rapeseed oil, rice bran oil, safflower oil, sasanqua oil, soybean oil, sunflower seed oil, tall oil, tsubaki oil, vegetable oils, marine oils which can be converted into plastic or solid fats such as menhaden, candlefish oil, cod-liver oil, orange roughy oil, pile herd, sardine oil, whale and herring oils, and combinations thereof.

As mentioned hereinabove, the iodine value is a common measurement of the degree of unsaturation of an oil. In the present invention, higher iodine values may lead to a greater degree of crosslinking and may require less time to crosslink the oil. In embodiments, the base oil has an IV of from about 70 to more than about 170. In embodiments, the feedstock is a liquid at room temperature. In alternative embodiments, the feedstock is a solid at room temperature. In embodiments, the feedstock is a mixture of oils that are solid at room temperature and oils that are liquid at room temperature. In preferred embodiments, the base oil subjected to the present invention has an iodine value of above 120, more preferably above 130, more preferably above 135, and still more preferably above 140. In embodiments, the base oil is crude soy oil having an iodine value in the range of from about 130 to 135. In embodiments, the base oil comprises primarily triglyceride oil with an iodine value above about 70. In certain embodiments, this iodine value is above about 130. In other embodiments, the iodine value is above about 170. The base oil may be modified, such as by bleaching or deodorizing. The base oil may contain trace amounts of free fatty acids. Sources of base oils and methods used to make base oils are known to those of skill in the art.

In embodiments, the base oil is derived from naturally occurring liquid oils such as sunflower oil, canola, soybean oil, olive oil, corn oil, peanut oil, safflower oil, high oleic sunflower oil, safflower oil, glycerol esters of purified fatty acid methyl esters, polyglycerol esters, and combinations thereof. Suitable liquid oil fractions may also be obtained from palm oil, lard, and tallow, for example, as by fractionation or by direct interesterification, followed by separation of the oil.

In embodiments, the feedstream comprises a plurality of oils and the ratios of the starting oils in the feedstream are modified to yield the desired fatty acid product composition and residual bottoms consistency in accord with the final disposition of the product.

The base oil may have a tendency to oxidize. In such instances, an antioxidant may be added to the base oil in line 15 (line 315 in FIG. 2). Some oils contain a natural antioxidant and others are naturally stable to oxidation. For the naturally stable oils, it may not be necessary to add an antioxidant. The amount of antioxidant added depends on several factors including the end use of the oil, the temperature, pressure, and amount of oxygen to which the oil will be exposed, as well as the duration of exposure. In embodiments, the base oil comprises antioxidant in the range of from about 0.1% to about 0.5% by weight.

A wide variety of antioxidants are suitable for use, including but not limited to tocopherol, butylated hydroxytoluene (BHT), butylated hydroxyanisole (BHA), tertiary butylhydroquinone (TBHQ), ethylenediaminetetracetic acid (EDTA), gallate esters (i.e. propyl gallate, butyl gallate, octyl gallate, dodecyl gallate, etc.), tocopherols, citric acid, citric acid esters (i.e. isopropyl titrate, etc.), gum guaiac, nordihydroguaiaretic acid (NDGA), thiodipropionic acid, ascorbic acid, ascorbic acid esters (i.e. ascorbyl palmitate, ascorbyl oleate, ascorbyl stearate, etc.) tartaric acid, lecithin, methyl silicone, polymeric antioxidant (Anoxomer) plant (or spice and herb) extracts (i.e. rosemary, sage, oregano, thyme, marjoram, etc.), and mixtures thereof. In embodiments, the antioxidant is ascorbyl palmitate. In embodiments, the antioxidant is ascorbyl palmitate in combination with tocopherol.

Heater 35 (335 in FIG. 2) is used to preheat the base oil, and pump 15 (315) is used to pump base oil into reactor 60 (360 in FIG. 2). The base oil introduced into the reactor is heated, for example, via heat exchanger 80 in FIG. 1, or heating mantle 380 in FIG. 2. The base oil is heated under inert conditions under vacuum provided by vacuum pump 180. Inert gas may be introduced into reactor 60 via line 50. The inert gas used to purge reactor 60 may be nitrogen. Vacuum pump 180 is used to vacuum strip the fatty acids obtained in the scission/hydrolysis reaction from the bottoms residue which comprises cross-linked product. Stripped fatty acids may exit reactor 60 via gas line 70, while bottoms product may exit reactor 60 via line 90.

Not to be limited by theory, it is believed that the heating process of the present invention results in chain scission and cross linking. Chain scission results in lower carbon number fractions of fatty acids that can then be fractionated, as further discussed hereinbelow. As used herein, scission can be breaking of the carbon-carbon single or double bond on the fatty acid group. In some embodiments, reactor 60 contains a catalyst effective to enhance the cross-linking and/or fatty acid splitting of the triglyceride oil. U.S. Pat. No. 6,696,581, for example, describes the use of precious metal catalyst in solvent to cross-link fatty acids and theorizes the mechanisms of such cross-linking.

The heating and vacuum reaction may be conducted in batch, continuous or semi-continuous mode depending on the needs of the user. In embodiments, semi-continuous and continuous operation allow for perpetual processing by continuous introduction of starting materials (e.g. base oil and/or catalyst) to the reaction and extraction of fatty acids by vacuum stripping. For example, as indicated in FIG. 1, crosslinking may be performed as a continuous process.

The base oil may be heated to a temperature suitable for obtaining the desired volatilized fatty acids. In embodiments, the base oil is heated to a temperature in the range of from about 250° C. to about 450° C. In embodiments, reactor 60 is operated at a temperature in the range of from about 200° C. to about 600° C. In alternative embodiments, the temperature within reactor 60 is in the range of from about 300° C. to about 400° C. In still other embodiments, the temperature within reactor 60 is in the range of from about 310° C. to about 375° C.

Vacuum pump 180 creates a vacuum of between 1 kPa (0.01 atm) to 50 kPa (0.5 atm) in reactor 60. The feedstock comprising triglyceride may be heated for a time in the range of from about 0.5 to about 5 hours. In embodiments, the process is performed batchwise over a time of from about 0.1 hours to about 8 hours. In other embodiments, the time range for batch operation is from about 1 hour to about 3 hours. In still other embodiments, the time for batch operation is about 2 hours.

Within reactor 60, lighter fatty acids are volatilized and the oil is cross-linked. The vacuum strips the lighter volatile fatty acid which may exit reactor 60 via line 70.

In embodiments, water is introduced into reactor 60 to help promote a hydrolysis reaction in addition to the scission reaction. In embodiments, the heating and vacuum reaction incorporates agitation and/or countercurrent flow with water to increase the efficiency of the reaction. This may be effected by mechanical means or by a countercurrent method, for example, analogous to that described in the Colgate-Emery method.

In the embodiment of FIG. 1, volatilized lower molecular weight fatty acids stripped from the base oil in reactor 60 are introduced via line 70 into condenser 110. Condensed fatty acids in the condensate of condenser 110 are introduced into accumulator 130 via line 115.

Vacuum Stripped Fatty Acid Product. The fatty acid product in line 115 may have a carbon number distribution between 6 and 20. In embodiments, the carbon number is between 8 and 16. In embodiments, the fatty acid condensate is fractionated, for example by means of heat and vacuum, to yield narrow carbon number products. Thus, in embodiments, the process of the invention further includes separating the free fatty acids into fractions defined by carbon numbers, as known to those of skill in the art. Common methods of separation include, by way of example, centrifugation, distillation, and settling. For example, as shown in FIG. 1, accumulator 130 is fluidly connected with fractionator 150 via line 140. Heat exchanger 160 is used to heat fractionator 150 and fractionate fatty acids. Fatty acids boiling below the temperature within fractionator 150 exit as gas in line 155, and fatty acids remaining liquid may be removed via line 170. Fractionator 150 may be, for example, a distillation column.

In the embodiment of FIG. 2, reactor 360 serves primarily as a heated holding tank. Product from reactor 360 is introduced via line 385 into wiped film evaporator, WFE, 400. In this embodiment, condensate comprising fatty acids of differing carbon chain lengths are fractionated by means of a wiped film evaporator. A wiped film evaporator (WFE) 400 can be used in a continuous process where carefully controlled temperatures and pressures can be used to fractionate specific carbon number ranges based on boiling points. In the embodiment of FIG. 2, WFE 400 is used to separate fatty acids which exit WFE 400 via line 370 from the cross-linked mix which exits WFE 400 via line 390. Combinations of WFE 400 with Fractionators 150 may also be used.

In embodiments, the fatty acid products of this invention are further processed to produce low degree of unsaturation, low trans-isomer fatty acid. In embodiments, this further processing comprises coupling the scission/hydrolysis reaction described herein with saturated fatty acid removal. In embodiments, saturated fatty acids are removed from condensate 140 via low temperature crystallization. In low temperature crystallization, the fatty acid product in line 140 (FIG. 1) or line 370 (FIG. 2) may be mixed with a polyglycerol ester crystal modifier and the mixture subjected to winterization in order to separate saturated fatty acids from unsaturated fatty acids. As used herein, the term "winterization" refers to the process of cooling oil to low temperatures until the high melting point molecules form solid particles large enough to be removed by filtration or centrifugation. Winterization is a specialized form of the overall process of fractional crystallization. In certain embodiments, the winterizing may be conducted in a batch reactor, a continuous reactor or a semi-continuous reactor.

In alternative embodiments, the fatty acids produced by the methods of the present invention are further processed by hydrogenation. As used herein, hydrogenation refers to the addition of hydrogen to double bonds of unsaturated fatty acids. This may be carried out by reacting the liquid fatty acid condensate with gaseous hydrogen at elevated temperatures and pressures. In embodiments, high shear, as described herein with regard to hydrogenation of BCR, is incorporated into the hydrogenation of the unsaturated fatty acids to enhance the hydrogenation thereof.

In embodiments, the stripped fatty acids are further processed into fatty acid esters by reacting with alcohol through means known to those in the art. In embodiments, stripped fatty acids are converted to fatty amines by reaction with amines by methods known to those experienced in the art.

In embodiments, fatty acid fractions are processed to separate out sterols that are inherent in small quantities in oils extracted from plants and animals utilizing solvents or pressing techniques. Lecithin or phosphatidylcholine (a phospholipid which upon hydrolysis yields two fatty acids molecules and a molecule each of glycerophosphoric acid and choline) may also be separated from the bottoms and/or vacuum condensate.

In embodiments, the stripped fatty acids have a low percentage of trans-isomer fatty acids. In embodiments, the stripped fatty acids comprise less than about 6 weight percent trans-isomers. In embodiments, the stripped fatty acids comprise less than about 30 weight percent C18 content.

In embodiments, the vacuum stripped fatty acids are useful in the food, pharmaceutical, chemical, plastics and cosmetics industries. For example, the fatty acids may be food grade and may be useful as binder/tackifier for pills/tablets. Fatty acids can undergo esterification, amidation, nitrile and salt formation. As an example the sodium salt of fatty acid is a primary ingredient of bar soap. Fatty acid amides and esters are used as plastic processing aids.

Production of Wax Alternatives from BCR. The residual material that is not vacuum stripped in reactor 60 or WFE 400 is herein referred to as 'bottoms,' 'bottoms cross-linked residue,' or BCR. In embodiments, the cross-linked residual bottoms comprise mono-, di-, tri-, tetra-, or penta-glycerides and/or esters. Fatty acid dimers and trimers may also be present due to cross-linking of free fatty acid groups. The BCR may have an iodine value below about 110. In embodiments, the iodine value of the BCR is below about 50 and, in other embodiments, below about 10.

In embodiments, the residue phase in line 90 (390 in FIG. 2), comprises mainly mono-acylglycerides, di-acylglycerides and tri-acylglycerides and is further processed to extract additional fatty acids. In embodiments, this further processing includes recycling at least a portion of the residue product in line 90 (line 390 in FIG. 2) back through the hydrolysis/scission process via recycle, e.g. recycle stream 95 in FIG. 1. Recycle stream 95 may be introduced into line 15 either upstream or downstream of heater 135. In batch embodiments, the residue phase remaining in batch reactor 60 may be combined with additional glycerol fatty acid ester-containing composition prior to further heating.

In another embodiment, the bottoms comprising residual cross-linked triglycerides, diglycerides and monoglycerides are utilized as feedstock for hydrogenation, either alone or blended with additional triglycerides. The cross-linked bottoms obtained upon vacuum stripping of the fatty acids may be combined with an unsaturated oil and subjected to hydrogenation, whereby enhanced hydrogenated vegetable oil waxes may be produced. Addition of bottoms from the present invention to a hydrogenation feedstock oil may beneficially modify the properties of the hydrogenated vegetable oil product. The enhanced hydrogenated product (hereinafter EHP) may be used as a partial or complete substitute for petroleum wax and petroleum wax blends. In embodiments, the addition of bottoms to hydrogenation feedstock oil results in plasticizing of the finished vegetable oil wax rendering it suitable as an alternative to petroleum waxes such as petrolatum and microcrystalline wax as well as conventional paraffin wax.

Hydrogenation of a feedstock oil comprising bottoms residue may be performed by any means known to those in the art. In embodiments, hydrogenation is carried out by reacting the bottoms with gaseous hydrogen at elevated temperature and pressure. In embodiments, high shear is utilized to enhance the hydrogenation of an oil comprising residual cross-linked bottoms. In embodiments, an external high shear mixer is used to accelerate the hydrogenation reaction. In such embodiments, hydrogen, hydrogenation feedstock, and optionally catalyst are mixed in a high shear mixer and introduced to a vessel 10 where the reaction conditions are controlled over time until a desired IV value is reached.

Hydrogenation of a feedstock oil comprising bottoms residue utilizing high shear will now be discussed with reference to FIG. 1. Line 90 is fluidly connected to line 21 whereby at least a portion of the BCR in line 90 may be introduced into HSD 40. In this manner, hydrogenation feedstock in line 13 may comprise from 1 weight percent to 100 weight percent BCR and from 0 weight percent to about 99 weight percent of an unsaturated base oil, which may be introduced via line 21. In operation for the hydrogenation of a feedstock comprising BCR, a dispersible hydrogen-containing gas stream is introduced into line 22, and combined in line 13 with the hydrogenation feedstock comprising BCR. The hydrogen-containing gas may be substantially pure hydrogen, or a gas stream comprising hydrogen.

In embodiments, the hydrogen-containing gas is fed directly into HSD 40, instead of being combined with the liquid hydrogenation feedstock in line 13. Pump 5 may be operated to pump the hydrogenation feedstock and to build pressure and feed HSD 40, providing a controlled flow throughout high shear device (HSD) 40. In some embodiments, pump 5 increases the pressure of the HSD inlet stream to greater than 202.65 kPa (2 atm), preferably greater than about 303.975 kPa (3 atmospheres). In this way, high shear may be combined with pressure to enhance reactant intimate mixing and hydrogenation.

In embodiments, reactants and, if present, catalyst (for example, aqueous solution, and catalyst) are first mixed in vessel 10. Reactants enter vessel 10 via, for example, inlet lines (not shown in FIG. 1). Any number of vessel 10 inlet lines is envisioned. In an embodiment, vessel 10 is charged with catalyst and the catalyst if required, is activated according to procedures recommended by the catalyst vendor(s).

After pumping, hydrogen and hydrogenation feedstock in line 13 are mixed within HSD 40, which serves to create a fine dispersion of the hydrogen-containing gas in the hydrogenation feedstock. In HSD 40, the hydrogen-containing gas and hydrogenation feedstock are highly dispersed such that nanobubbles, submicron-sized bubbles, and/or microbubbles of hydrogen are formed for superior dissolution into solution and enhancement of reactant mixing. For example, disperser IKA® model DR 2000/4, a high shear, three stage dispersing device configured with three rotors in combination with stators, aligned in series, may be used to create the dispersion of dispersible hydrogen-containing gas in liquid phase comprising hydrogenation feedstock (i.e., "the reactants"). The rotor/stator sets may be configured as illustrated in FIG. 3, for example. The combined reactants enter the high shear device via line 13 and enter a first stage rotor/stator combination. The rotors and stators of the first stage may have circumferentially spaced first stage rotor teeth and stator teeth, respectively. The coarse dispersion exiting the first stage enters the second rotor/stator stage. The rotor and stator of the second stage may also comprise circumferentially spaced rotor teeth and stator teeth, respectively. The reduced bubble-size dispersion emerging from the second stage enters the third stage rotor/stator combination, which may comprise a rotor and a stator having rotor teeth and stator teeth, respectively. The dispersion exits the high shear device via line 18. In some embodiments, the shear rate increases stepwise longitudinally along the direction of the flow, 260.

For example, in some embodiments, the shear rate in the first rotor/stator stage is greater than the shear rate in subsequent stage(s). In other embodiments, the shear rate is substantially constant along the direction of the flow, with the shear rate in each stage being substantially the same.

If the high shear device 40 includes a PTFE seal, the seal may be cooled using any suitable technique that is known in the art. For example, the reactant stream flowing in line 13 or line 21 may be used to cool the seal and in so doing be preheated as desired prior to entering high shear device 40.

The rotor(s) of HSD 40 may be set to rotate at a speed commensurate with the diameter of the rotor and the desired tip speed. As described above, the high shear device (e.g., colloid mill or toothed rim disperser) has either a fixed clearance between the stator and rotor or has adjustable clearance. HSD 40 serves to intimately mix the hydrogen-containing gas and the hydrogenation feedstock. In some embodiments of the process, the transport resistance of the reactants is reduced by operation of the high shear device such that the velocity of the reaction is increased by greater than about 5%. In some embodiments of the process, the transport resistance of the reactants is reduced by operation of the high shear device such that the velocity of the reaction is increased by greater than a factor of about 5. In some embodiments, the velocity of the reaction is increased by at least a factor of 10. In some embodiments, the velocity is increased by a factor in the range of about 10 to about 100 fold.

In some embodiments, HSD 40 delivers at least 300 L/h at a tip speed of at least 4500 ft/min, and which may exceed 7900 ft/min (40 m/s). The power consumption may be about 1.5 kW. Although measurement of instantaneous temperature and pressure at the tip of a rotating shear unit or revolving element in HSD 40 is difficult, it is estimated that the localized temperature seen by the intimately mixed reactants is in excess of 500° C. and at pressures in excess of 500 kg/cm$^2$ under cavitation conditions. The high shear mixing results in dispersion of the hydrogen-containing gas in micron or submicron-sized bubbles. In some embodiments, the resultant dispersion has an average bubble size less than about 1.5 μm. Accordingly, the dispersion exiting HSD 40 via line 18 comprises micron and/or submicron-sized gas bubbles. In some embodiments, the mean bubble size is in the range of about 0.4 μm to about 1.5 μm. In some embodiments, the resultant dispersion has an average hydrogen bubble size less than 1 μm. In some embodiments, the mean bubble size is less than about 400 nm, and may be about 100 nm in some cases. In many embodiments, the microbubble dispersion is able to remain dispersed at atmospheric pressure for at least 15 minutes.

Once dispersed, the resulting gas/liquid or gas/liquid/solid (in cases where solid catalyst slurry loop is utilized) dispersion exits HSD 40 via line 18 and feeds into vessel 10, as illustrated in FIG. 1. As a result of the intimate mixing of the reactants prior to entering vessel 10, a significant portion of the chemical reaction may take place in HSD 40, with or without the presence of a catalyst. Accordingly, in some embodiments, reactor/vessel 10 may be used primarily for heating and separation of unreacted hydrogen gas from the enhanced hydrogenated product and recycling this hydrogen back to the inlet of the HSD. Alternatively, or additionally, vessel 10 may serve as a primary reaction vessel where most of the hydrogenation occurs. For example, in embodiments, vessel 10 is a fixed bed reactor comprising a fixed bed of hydrogenation catalyst.

Vessel/reactor 10 may be operated in either continuous or semi-continuous flow mode, or it may be operated in batch mode. The contents of vessel 10 may be maintained at a specified reaction temperature using heating and/or cooling capabilities (e.g., cooling coils) and temperature measurement instrumentation. Pressure in the vessel may be monitored using suitable pressure measurement instrumentation, and the level of reactants in the vessel may be controlled using a level regulator (not shown), employing techniques that are known to those of skill in the art. The contents may be stirred continuously or semi-continuously.

Catalyst. If a catalyst is used to promote hydrogenation, the catalyst may be introduced into vessel 10 as a slurry or catalyst stream. Alternatively, or additionally, catalyst may be added elsewhere. For example, in embodiments, catalyst slurry may be injected directly into line 21. In embodiments, vessel/reactor 10 comprises any catalyst known to those of skill in the art to be suitable for hydrogenation. In embodiments, a nickel hydrogenation catalyst is utilized.

The bulk or global operating temperature of hydrogenation feedstock reactant is desirably maintained below the flash point. In some embodiments, the operating conditions for high shear hydrogenation comprise a temperature in the range of from about 100° C. to about 230° C. In embodiments, the temperature is in the range of from about 160° C. to 180° C. In specific embodiments, the reaction temperature in vessel 10, in particular, is in the range of from about 155° C. to about 160° C. In some embodiments, the reaction pressure in vessel 10 is in the range of from about 202.65 kPa (2 atm) to about 5.6 MPa-6.1 MPa (55-60 atm). In some embodiments, reaction pressure is in the range of from about 810.6 kPa to about 1.5 MPa (8 atm to about 15 atm). In embodiments, vessel 10 is operated at or near atmospheric pressure.

Optionally, the dispersion in line 18 may be further processed prior to entering vessel 10, if desired. In vessel 10, hydrogenation occurs/continues via reaction with hydrogen. The contents of the vessel may be stirred continuously or semi-continuously, the temperature of the reactants may be controlled (e.g., using a heat exchanger), and the fluid level inside vessel 10 may be regulated using standard techniques. Hydrogenated product may be produced either continuously, semi-continuously or batch wise, as desired for a particular application. Excess unreacted hydrogen gas may exit vessel 10 via gas line 17. In embodiments the reactants and conditions are selected so that the gas stream in line 17 comprises less than about 6% unreacted hydrogen by weight. In some embodiments, the reaction gas stream in line 17 comprises from about 1% to about 4% hydrogen by weight. The reaction gas removed via line 17 may be further treated, and the unreacted hydrogen may be recycled, as desired, for example to HSD 40.

Enhanced hydrogenated product (hereinafter EHP) exits vessel 10 by way of line 16. The EHP may be suitable as an alternative to petroleum-based waxes such as paraffin and microcrystalline waxes in applications including adhesives, candles, paper coatings, fire logs, particle board, composite board, asphalt modification, fruit coating, gypsum board, cable filling, cosmetics as replacements for petrolatum, as plastic lubricants in PVC and other applications where petroleum waxes are conventionally utilized. Embodiments of this aspect of the present disclosure include compositions comprising blends of EHPs or residual cross-linked triglycerides, diglycerides and monoglycerides with petroleum or other naturally occurring waxes. The attributes derived from the addition of the EHPs may include flexibility, tack and/or hardness modification. Replacement of from 1% to 100% by weight of a petrolatum or micro-crystalline wax material may be made. As opposed to conventional hydrogenated triglycerides which tend to become hard and brittle as hydrogenation levels are increased (as iodine value decreases), the EHPs according to embodiments of this disclosure may overcome these deficiencies.

As mentioned above, the EHP may be formed by hydrogenation of a hydrogenation feedstock comprising from 1 weight percent to 100 weight percent bottoms cross-linked residue (for example, from line 90 in FIG. 1 or line 390 in FIG. 2 or from reactor 60 following batchwise removal of fatty acids) and from 0 weight percent to 99 weight percent of an unhydrogenated or partially hydrogenated base oil. The amount of BCR may be adjusted to alter the melting point of the resulting EHP to within a desired range. In embodiments, the EHP has a melting point of from about 40° C. to 50° C. (110° F. to 120° F.); in embodiments, the EHP has a melting point of from about 70° C. to about 75° C. (160° F. to about 165° F.). In embodiments, EHP suitable for use as, for example, candle wax as the brittleness is decreased by the presence of the BCR in the hydrogenation feedstock.

In embodiments, from 1 weight percent to 99 weight percent EHP is blended with from 99 weight percent to 1 weight percent of a traditional paraffin wax. The addition of the EHP to traditional paraffin wax may serve as a tackifier/binder in place of conventional tackifiers and binders, such as ethylene vinyl acetate (EVA). The use of EHP in place of traditional chemical binders is desirable, as the EHP is biodegradable. Also, the EHP may be food grade, and the wax suitable for edible purposes, such as for coating produce boxes.

In another embodiment, esters such as mono-, di-, tri-, tetra-, or penta-ester can be added to modify or enhance the desired physical characteristics of the final composition.

In some embodiments it may be desirable to pass the contents of vessel 10, or a liquid fraction containing unsaturated oil, through HSD 40 during a second pass. In this case, line 16 may be connected to line 21 as indicated by line 20, such that at least a portion of the contents of line 16 is recycled from vessel 10 and pumped by pump 5 into line 13 and thence into HSD 40. Additional hydrogen-containing gas may be injected via line 22 into line 13, or it may be added directly into the high shear device (not shown). In other embodiments, product stream in line 16 may be further treated (for example, separation of saturated product therefrom) prior to recycle of a portion of the unsaturated liquid in the product stream being recycled to high shear device 40.

In some embodiments, two or more high shear devices like HSD 40, or configured differently, are aligned in series, and are used to further enhance the hydrogenation reaction. The operation of multiple devices may be in either batch or continuous mode. In some instances in which a single pass or "once through" process is desired, the use of multiple high shear devices in series may also be advantageous. In some embodiments where multiple high shear devices are operated in series, vessel 10 may be omitted. For example, in embodiments, outlet dispersion in line 18 may be fed into a second high shear device. When multiple high shear devices 40 are operated in series, additional hydrogen gas may be injected into the inlet feedstream of each device. In some embodiments, multiple high shear devices 40 are operated in parallel, and the outlet dispersions therefrom are introduced into one or more vessel 10.

Features. In embodiments, the fatty acids and "bottoms" produced via the disclosed system and methods are more stable than conventionally-obtained products due to the reduced degree of unsaturation therein. In embodiments, the stripped fatty acids obtained via the disclosed method have superior product appearance relative to fatty acids obtained via conventional triglyceride hydrolysis. The stripped fatty acids may be light in color as measured by the Gardner color scale (ASTM test method D1544). In embodiments, the stripped fatty acids are essentially colorless. In embodiments, the stripped fatty acids obtained via the disclosed method have superior stability relative to fatty acids obtained via conventional triglyceride hydrolysis as measured by iodine values and the corresponding lower degree of unsaturation in the fatty acid.

The application of enhanced mixing of the hydrogen and hydrogenation feedstock within HSD 40 potentially permits faster and/or more complete hydrogenation of the hydrogenation feedstock. In some embodiments, the enhanced mixing potentiates an increase in throughput of the process stream. In some embodiments, the high shear mixing device is incorporated into an established process, thereby enabling an increase in production (i.e., greater throughput). In contrast to some methods that attempt to increase the degree of hydrogenation by simply increasing reactor pressures, the superior dispersion and contact provided by external high shear mixing may allow in many cases a decrease in overall operating pressure while maintaining or even increasing reaction rate. Without wishing to be limited to a particular theory, it is believed that the level or degree of high shear mixing is sufficient to increase rates of mass transfer and also produces localized non-ideal conditions that permit reactions to occur that would not otherwise be expected to occur based on Gibbs free energy predictions. Localized non ideal conditions are believed to occur within the high shear device resulting in increased temperatures and pressures with the most significant increase believed to be in localized pressures. The increase in pressures and temperatures within the high shear device are instantaneous and localized and quickly revert back to bulk or average system conditions once exiting the high shear device. In some cases, the high shear mixing device induces cavitation of sufficient intensity to dissociate one or more of the reactants into free radicals, which may intensify a chemical reaction or allow a reaction to take place at less stringent conditions than might otherwise be required. Cavitation may also increase rates of transport processes by producing local turbulence and liquid micro-circulation (acoustic streaming). An overview of the application of cavitation phenomenon in chemical/physical processing applications is provided by Gogate et al., "Cavitation: A technology on the horizon," *Current Science* 91 (No. 1): 35-46 (2006). The high shear mixing device of certain embodiments of the present system and methods induces cavitation whereby hydrogen and triglycerides are dissociated into free radicals, which then react to produce enhanced hydrogenated product.

The increased surface area of the micrometer sized and/or submicrometer sized hydrogen bubbles in the dispersion in line 18 produced within high shear device 40 results in faster and/or more complete reaction of hydrogen gas with unsaturated oil in the hydrogenation feedstock introduced via line 13. As mentioned hereinabove, additional benefits are the ability to operate vessel 10 at lower temperatures and pressures resulting in both operating and capital cost savings. The benefits of the use of high shear in the hydrogenation include, but are not limited to, faster cycle times, increased throughput, reduced operating costs and/or reduced capital expense due to the possibility of designing smaller hydrogenation reactors, and/or operating the hydrogenation reactor at lower temperature and/or pressure.

The use of an external high shear mechanical device provides rapid contact and mixing of hydrogen and hydrogenation feedstock in a controlled environment in the reactor/high shear device. The high shear device reduces the mass transfer limitations on the hydrogenation reaction and thus may increase the overall reaction rate, reduce the amount of unreacted hydrogen, increase the degree of saturation in the enhanced hydrogenation product, and/or allow substantial hydrogenation under global operating conditions under which substantial reaction may not be expected to occur.

EXAMPLES

Example 1

Fractionating Fatty Acids from Triglycerides

A system comprising a reactor 60, a condenser 110, an accumulator 130, and a vacuum pump 180 as shown in FIG. 1 was utilized to produce fatty acids from non-hydrogenated soy oil. The reactor 60 was a spherical 12 liter/3 neck glass flask equipped with a stirrer. The stirrer was a magnetic stirring bar 3"×¾" that was used to mix the contents of reactor flask 60 during the reaction and cooling. The flask reactor 60 was operated in batch mode (with no liquid line 90 in this embodiment) and heating device 80 was a heating mantle positioned around the body of reactor flask 60.

Base non-hydrogenated soy oil that was refined but not deodorized or bleached was sourced from ADM Corp, Decatur, Ill. In the examples contained herein the fatty acid composition of the triglycerides was obtained using AOCS Official Method Ce 2-66 (American Oil Chemists' Society (AOCS) 2211 W. Bradley Ave., Champaign, Ill.). The iodine value was determined by the AOCS Recommended Practice Cd 1c-85. Analysis of the base oil is presented in Table 2.

TABLE 2

Base Oil Composition

| | Weight Percent, % |
|---|---|
| Fatty Acid | |
| C18-0 | 4.6 |
| C18-1 | 23.8 |
| C18-2 | 52.4 |
| C18-3 | 6.8 |
| Trans Fat | |
| C18-1 trans | 0 |
| C18-2 trans | 0.2 |
| C18-3 trans | 0.5 |
| Total Trans | 0.7 |
| IV (cg iodine/gm) | 129.6 |

A volume of 7.57 L (2 gallons) of base oil whose composition is presented in Table 2 was placed in reactor 60. The oil was heated to 320° C. and maintained for 3 hours with stirring. Nitrogen was introduced into reactor flask 60 via inert gas line 50 and bubbled through reactor flask 60 to maintain inert condition. At the end of 3 hours, heating mantle 80 was turned off and vacuum pump 180 was used to pull a vacuum 101.6 kPa (30 inch Hg) on condenser 110 while the oil cooled by convection to 200° C.

The condensate (collected in accumulator 130) was approximately 700 mL. The condensate and bottoms (residual in 12 liter reactor flask 60) were analyzed by AOCS method Celc 89 and iodine value by method USP/NF 401. The measurement of cis and trans isomers was performed in accordance with test methods as described in AOCS Official Method Ce 1c-89. The results are presented in Table 3.

TABLE 3

Fatty Acid Composition

| Component | BCR (Bottoms) | Condensate (Light Fatty Acids) |
|---|---|---|
| C6 | — | 11.1 |
| C8 | — | 3.7 |
| C10 | 1.5 | 9.6 |
| C12 | — | 1.0 |
| C14 | — | 2.2 |
| C15 | — | — |
| C15-1 | 0.4 | .07 |
| C16 | 16.9 | 11.6 |
| C16-1 | 0.3 | — |
| C17 | 0.3 | 1.2 |
| C17-1 | — | — |
| C18 | 10.3 | 3.1 |
| C18-1 | 45.9 | 13.4 |
| C18-2 | 18.7 | 10.5 |
| C18-3 | — | — |
| C-20 | 1.1 | 0.5 |
| C20-1 | — | — |
| C-22 | 0.8 | — |
| C22-1 | 0.8 | — |
| C-24 | 0.8 | — |
| Others | 2.2 | 30.3 |
| C18-1 trans | 10.5 | 2.8 |
| C18-2 trans | 3.5 | 2.3 |
| C18-3 trans | — | — |
| Iodine Value | 72.1 | 29.7 |

The results show a significant reduction in iodine value relative to the base oil (77% reduction in iodine value for 'bottoms' and 44% reduction for condensate) indicating a reduction in the number of double bonds present. The results also indicate a significant reduction in the C18 content of the condensate.

Example 2

Hydrogenation of Hydrogenation Feedstock Oil Comprising BCR

The BCR from Example 1 was mixed with RBD (refined, bleached and deodorized) soy oil at varying ratios of cross-linked bottoms residue and hydrogenated. The properties of the enhanced hydrogenated wax product were investigated. Purified Grade II hydrogen gas having a purity of 99.9% (+) (Standard: IS:HY 200) was obtained from Airgas Corp. The hydrogen was fed through a pressure relief valve via pipe line to coil in autoclave for mixing in oil.

The following procedure was used to hydrogenate the triglyceride blends. Non-hydrogenated vegetable oil and indicated level of bottoms were placed into a pressure reactor equipped with an electric heating mantle, stirrer (agitator), gas inlet and outlet, temperature probe and pressure gauge. A reactor (2 liter reactor manufactured by Parr Inc, Moline, Ill.) was charged with vegetable oil and nickel catalyst 2% w/w (NYSOFACT®120 from BASF Catalysts LLC, Erie, Pa.). The reactor was purged with nitrogen and/or hydrogen. The vegetable oil was heated to reaction temperature. Hydrogen injection at temperature was continued for one hour. Heating was discontinued and the reactor cooled by blowing air over the reactor and stopping hydrogen flow. Cooling was discontinued when ambient temperature was attained. Product was removed from the reactor and analyzed. The results of runs wherein the RBD oil was mixed with 25%, 10%, and 5% bottoms cross-linked residue obtained from Example 1 are shown in Table 4.

TABLE 4

Hydrogenation of RBD Containing Bottoms Cross-Linked Residue

| | Percent Bottoms, % | | |
|---|---|---|---|
| | 25 | 10 | 5 |
| Viscosity @ 100° C., cSt (D-445) | 10.28 | 10.51 | 10.42 |
| Drop Melt point, ° C. (° F.), (D-127) | 57.8 (136.0) | 53.3 (128.0) | 60.0 (140.0) |
| Color (D-1500) | 0.2 | 0.2 | 0.2 |

As seen in Table 4, the enhanced hydrogenated wax produced by blending bottoms with base oil followed by hydrogenation exhibit characteristics and physical properties comparable to petroleum-derived waxes and are suitable for use in replacement of petroleum waxes in adhesives, candles, paper coatings, fire logs, particle board, composite board, asphalt modification, fruit coating, gypsum board, cable filling, cosmetics as replacements for petrolatums, as plastic lubricants in PVC and other applications where petroleum waxes are utilized.

While preferred embodiments of the invention have been shown and described, modifications thereof can be made by one skilled in the art without departing from the spirit and teachings of the invention. The embodiments described herein are exemplary only, and are not intended to be limiting. Many variations and modifications of the invention disclosed herein are possible and are within the scope of the invention. Where numerical ranges or limitations are expressly stated, such express ranges or limitations should be understood to include iterative ranges or limitations of like magnitude falling within the expressly stated ranges or limitations (e.g., from about 1 to about 10 includes, 2, 3, 4, etc.; greater than 0.10 includes 0.11, 0.12, 0.13, and so forth). Use of the term "optionally" with respect to any element of a claim is intended to mean that the subject element is required, or alternatively, is not required. Both alternatives are intended to be within the scope of the claim. Use of broader terms such as comprises, includes, having, etc. should be understood to provide support for narrower terms such as consisting of, consisting essentially of, comprised substantially of, and the like.

Accordingly, the scope of protection is not limited by the description set out above but is only limited by the claims which follow, that scope including all equivalents of the subject matter of the claims. Each and every claim is incorporated into the specification as an embodiment of the present invention. Thus, the claims are a further description and are an addition to the preferred embodiments of the present invention. The disclosures of all patents, patent applications, and publications cited herein are hereby incorporated by reference, to the extent they provide exemplary, procedural or other details supplementary to those set forth herein.

What is claimed is:

1. A method of producing volatilized fatty acids, the method comprising:

heating a feedstock comprising at least one fat or oil in a reactor under inert vacuum to volatilize fatty acids, wherein said feedstock further comprises at least one antioxidant; and removing volatilized fatty acids from bottoms residue comprising cross-linked oil.

2. The method of claim 1 wherein the feedstock is selected from the group consisting of butterfat, cocoa butter, cocoa butter substitutes, illipe fat, kokum butter, milk fat, mowrah fat, phulwara butter, sal fat, shea fat, bomeo tallow, lard, lanolin, beef tallow, mutton tallow, other animal tallow, canola oil, castor oil, coconut oil, coriander oil, corn oil, cottonseed oil, hazelnut oil, hempseed oil, linseed oil, mango kernel oil, meadowfoam oil, Neatsfoot oil, olive oil, palm oil, palm kernel oil, palm olein, palm stearin, palm kernel olein, palm kernel stearin, peanut oil, rapeseed oil, rice bran oil, safflower oil, sasanqua oil, soybean oil, sunflower seed oil, tall oil, tsubaki oil, vegetable oils, marine oils, and combinations thereof.

3. The method of claim 2 wherein the feedstock comprises soybean oil.

4. The method of claim 1 wherein the feedstock has an iodine value of greater than 70.

5. The method of claim 1 wherein the at least one antioxidant comprises ascorbyl palmitate and tocopherol.

6. The method of claim 1 further comprising contacting the feedstock with a crosslinking catalyst during heating.

7. The method of claim 1 wherein heating is to a temperature in the range of from about 200° C. to about 600° C.

8. The method of claim 1 wherein the vacuum is in the range of from 1.0 kPa to about 50 kPa.

9. The method of claim 1 further comprising condensing the volatilized fatty acids to obtain a fatty acid condensate.

10. The method of claim 1 further comprising introducing water into the reactor to promote hydrolysis.

11. The method of claim 1 further comprising fractionating the fatty acids.

12. The method of claim 1 wherein removing volatilized fatty acids from bottoms residue is performed with a wiped film evaporator.

13. The method of claim 1 wherein less than about 6 weight percent of the volatilized fatty acids are trans-isomers.

* * * * *